(12) United States Patent
Teague et al.

(10) Patent No.: US 9,956,096 B2
(45) Date of Patent: May 1, 2018

(54) ASSEMBLY FOR TREATING BRANCHED VESSELS

(71) Applicant: Cook Medical Technologies LLC, Bloomington, IN (US)

(72) Inventors: James A. Teague, Spencer, IN (US); Larry Remington, Auburn, WA (US); Joel Ondersma, Bloomington, IN (US); Johnny LeBlanc, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days. days.

(21) Appl. No.: 13/967,679

(22) Filed: Aug. 15, 2013

(65) Prior Publication Data

US 2015/0051692 A1 Feb. 19, 2015

(51) Int. Cl.
*A61F 2/06* (2013.01)
*A61F 2/07* (2013.01)
*A61F 2/856* (2013.01)

(52) U.S. Cl.
CPC ............... *A61F 2/856* (2013.01); *A61F 2/07* (2013.01); *A61F 2002/061* (2013.01);
(Continued)

(58) Field of Classification Search
CPC .. A61F 2/07; A61F 2/865; A61F 2/954; A61F 2002/065; A61F 2002/067;
(Continued)

(56) References Cited

U.S. PATENT DOCUMENTS 5,609,627 A * 3/1997 Goicoechea ............... A61F 2/07
128/898
5,984,955 A * 11/1999 Wisselink ................. A61F 2/07
623/1.35
(Continued)

FOREIGN PATENT DOCUMENTS

WO    WO 03/099108 A2    12/2003
WO    WO 2008/107885 A2   9/2008

OTHER PUBLICATIONS

European Search Report dated Dec. 10, 2014 from corresponding application No. EP 14275163 (5 pages).
(Continued)

*Primary Examiner* — Darwin Erezo
*Assistant Examiner* — Katherine Schwiker
(74) *Attorney, Agent, or Firm* — Brinks Gilson & Lione

(57) ABSTRACT

This invention relates generally to an endoluminal prosthesis, and more particularly, to a stent graft assembly and method for treating branched vessels. The assembly comprises a first prosthesis having an overall shortened length comprising a main body formed of biocompatible graft material having a tapered proximal end. A bifurcated portion extends distally from the main body. The bifurcated portion comprises a first tubular portion defining a first lumen and a second tubular portion defining a second lumen. The assembly further comprises a second prosthesis having a tubular body of biocompatible graft material with a flared distal end portion. The flared distal end portion of the second prosthesis is configured to sealingly engage with the tapered main body of the first prosthesis.

10 Claims, 4 Drawing Sheets

(52) U.S. Cl.
CPC . *A61F 2002/067* (2013.01); *A61F 2230/0067* (2013.01); *A61F 2250/0039* (2013.01)

(58) Field of Classification Search
CPC .......... A61F 2002/075; A61F 2002/061; A61F 2230/0067; A61F 2250/0039; A61F 2/064; A61F 2002/072; A61F 2002/077; A61F 2/89; A61F 2/856; A61F 2002/826; A61F 2002/828
USPC ...................................... 623/1.13, 1.35, 1.16
See application file for complete search history.

(56) References Cited

U.S. PATENT DOCUMENTS

| | | | |
|---|---|---|---|
| 6,964,679 B1* | 11/2005 | Marcade et al. .............. | 623/1.13 |
| 8,945,200 B1* | 2/2015 | Eblacas .................. | A61F 2/954 |
| | | | 623/1.12 |
| 2002/0058986 A1* | 5/2002 | Landau .................. | A61F 2/064 |
| | | | 623/1.13 |
| 2004/0117003 A1* | 6/2004 | Ouriel ....................... | A61F 2/07 |
| | | | 623/1.35 |
| 2008/0046065 A1* | 2/2008 | Hartley et al. ............... | 623/1.13 |
| 2011/0087320 A1* | 4/2011 | Bolduc ................ | A61B 17/064 |
| | | | 623/1.35 |
| 2013/0274853 A1* | 10/2013 | Kelly ....................... | A61F 2/07 |
| | | | 623/1.11 |

OTHER PUBLICATIONS

Response to EPC communication dated Jun. 10, 2015 from corresponding application No. EP 14275163 (3 pages).

* cited by examiner

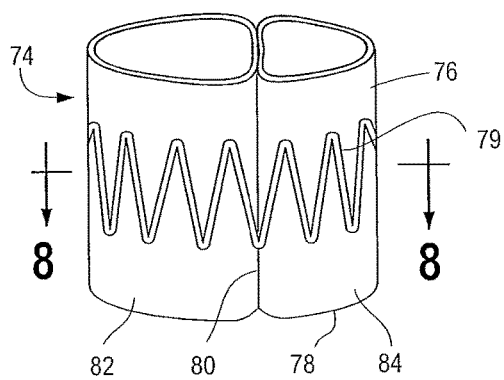
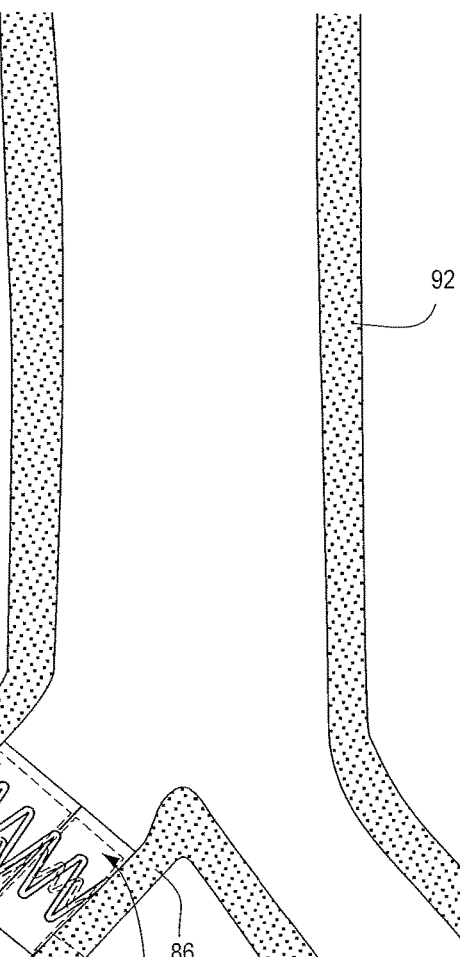
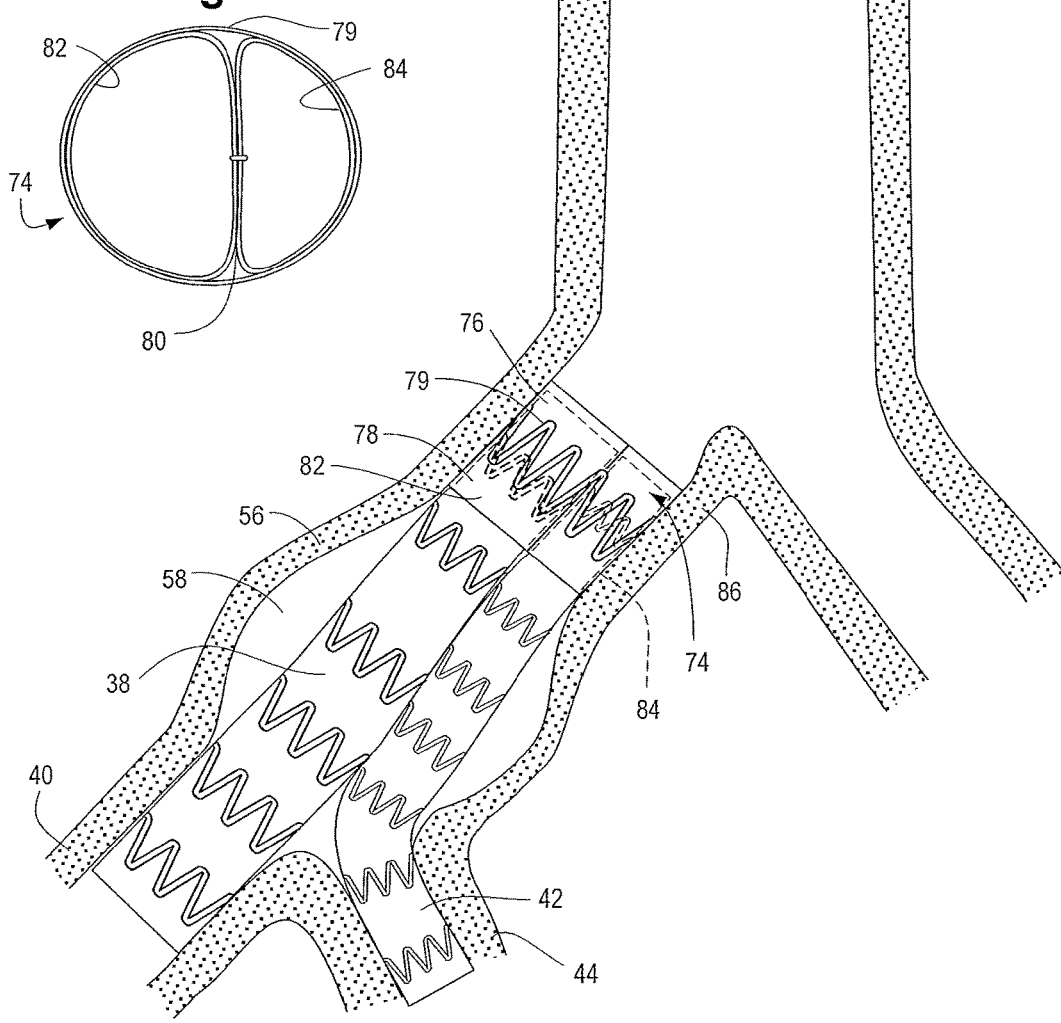

ASSEMBLY FOR TREATING BRANCHED VESSELS

BACKGROUND

This invention relates generally to medical devices, and more particularly, to endoluminal prostheses such as stent grafts and methods for treating branched vessels.

The functional vessels of human and animal bodies, such as blood vessels and ducts, occasionally weaken or even rupture. For example, a vessel wall can weaken, resulting in an aneurysm, or it may develop a tear in one of the layers of the wall resulting in a dissection.

One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic segments. They also may be a single tubular device or a bifurcated branching device depending on the desired application or the particular portion of the vasculature being treated.

In many cases, the damaged or defective portion of the vasculature may include a branch vessel extending from a main vessel. Fenestrated and/or branched endoluminal prostheses are known for treating such branch vessels. In one example, an iliac branch device may be placed in the common iliac artery. An iliac branch device generally consists of a main lumen which runs from the common iliac artery (CIA) to the external iliac artery (EIA) with a side branch extending from the main lumen and facing the internal iliac artery (IIA). The proximal end of the iliac branch device may connect directly to an AAA main body graft, or alternatively, the proximal end of the iliac branch device may be sealed to the AAA main body via an intermediate bridging limb.

Introduction of an iliac branch device and successful deployment of the iliac branch device may often depend upon a favorable layout of the arteries. However, the anatomy of the vasculature may be unique from one patient population to the next and also among individual patients. Anatomical limitations may restrict the patient base that is able to receive a branched graft, such as an iliac branch device, the chief limitation being the length of the common iliac artery (e.g. the measured distance from the main aortic bifurcation to the ostium of the internal iliac artery). In one example, branched stent grafts have been used to treat patients having common iliac arteries of a certain average length, such as approximately 40 mm in length or greater. The common iliac artery must be of a certain minimum length in order for the iliac branch device to seat properly, such that the fenestration and/or side branch is adjacent the ostium of the IIA while the proximal end of the iliac branch device does not extend above the aortic bifurcation, for example. However, the length of the common iliac arteries among certain patient populations, particularly in Asia, may be on average shorter, down to 20 mm in length or even less, such that treatment with a standard length iliac branch device may be difficult.

SUMMARY

A stent graft assembly is disclosed which accommodates the vasculature of diverse patient populations having unique layouts and varying geometries, including, but not limited to, patients having shorter than average length common iliac arteries. In one example, the stent graft assembly comprises a first prosthesis comprising a main body formed of biocompatible graft material having a proximal end and a distal end and a main lumen extending therebetween wherein the main lumen comprises a single lumen extending the length of the main body. A bifurcated portion extends distally from the main body, the bifurcated portion comprising a first tubular portion defining a first lumen and a second tubular portion defining a second lumen, wherein the first and second lumens are in communication with the main lumen and wherein the main body portion tapers inwardly from the bifurcated portion to the proximal end of the main body. The assembly further comprises a second prosthesis having a tubular body of biocompatible graft material having a flared distal end portion. The flared distal end portion of the second prosthesis is configured to sealingly engage with the tapered main body of the first prosthesis.

A method for treating a diseased vessel is also disclosed. In one example, the method comprises introducing a first prosthesis into a patient's vasculature. The first prosthesis comprises a main body formed of biocompatible graft material having a proximal end and a distal end and a main lumen extending therebetween wherein the main lumen comprises a single lumen extending the length of the main body. A bifurcated portion extends distally from the main body which comprises a first tubular portion defining a first lumen and a second tubular portion defining a second lumen, wherein the first and second lumens are in communication with the main lumen. The main body portion tapers inwardly from the bifurcated portion to the proximal end of the main body. The method further comprises positioning the first prosthesis in the common iliac artery, introducing a second prosthesis into the patient's vasculature wherein the second prosthesis comprises a tubular body of biocompatible graft material having flared distal end, and sealingly connecting the tapered main body of the first prosthesis and the flared distal end of the second prosthesis.

BRIEF DESCRIPTION OF THE DRAWINGS

FIG. 2a is a cross-sectional view of the bifurcated iliac device of FIG. 1a.

FIG. 7 illustrates an alternative example of a bifurcated iliac device according to the present disclosure suitable for treating isolated iliac aneurysms with connection stent grafts as shown in FIGS. 3 and 4, respectively, extending distally from the bifurcated iliac device.

FIG. 8 is a cross-sectional view of the bifurcated iliac device illustrated in FIG. 7.

FIG. 9 shows one example of a bifurcated iliac device as shown in FIG. 7 within the vasculature of a patient having an aneurysm in a common iliac artery.

DETAILED DESCRIPTION

Throughout this specification the terms proximal and proximally are used for a position or direction towards the patient's heart and the terms distal and distally are used for a position or direction away the patient's heart. The embodiments described below are in connection with the deployment of an implantable medical device, such as an endoluminal prosthesis, including, but not limited to stents, stent grafts, occlusion devices and the like. The term "branch vessel" refers to a vessel that branches off from a main vessel. Examples are the celiac and renal arteries which are branch vessels to the aorta, the aorta being the main vessel in this context. Furthermore, in the thoracic aorta there are branch vessels such as the brachiocephalic, carotid and subclavian arteries. As another example, the internal iliac is a branch vessel to the common iliac, the common iliac being the main vessel in this context. Thus, the terms "branch vessel" and "main vessel" are relative terms.

Figure 1A:
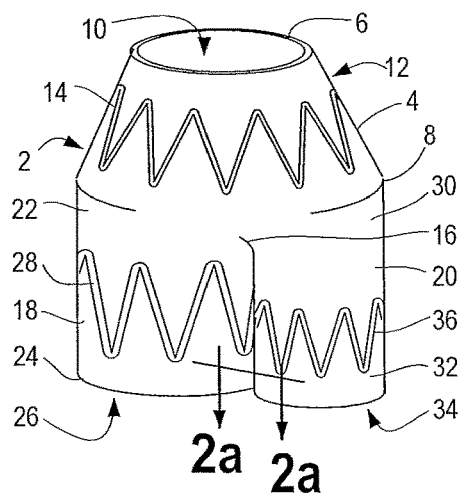
FIG. 1a shows a first example of a bifurcated iliac device according to the present disclosure.

Referring now to FIG. 1a, an exemplary prosthesis such as a stent graft is shown generally at 2. In one example, the stent graft 2 is preferably adapted for placement in the common iliac artery (CIA), and may be referred to herein as a bifurcated iliac device. However, it is also contemplated that the stent graft 2 may be placed in other branched vessels. The bifurcated iliac device 2 preferably includes a tubular main body portion 4 of biocompatible polymeric graft material having a proximal end 6 and a distal end 8 defining a main lumen 10 therebetween. Preferably, the lumen 10 at proximal end 6 is an inflow opening. The tubular body portion 4 preferably includes a proximal taper 12, such that the diameter narrows towards the proximal-most end 6. The taper 12 may range from about 14 mm to about 24 mm at its widest portion near distal end 8 of the tubular body 4 to about 12 mm at its most narrow (proximal) end 6. One or more stents 14 may be sutured or otherwise attached to the inside and/or outside of the main body portion 4 near the proximal end 6. Further stents may be positioned below the proximal end stent 14, and may be sutured or otherwise attached to the inside and/or the outside of the body portion 4.

Figure 1B:
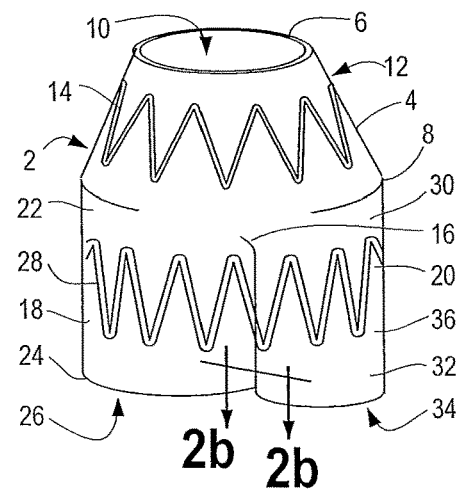
FIG. 1b shows a second example of a bifurcated iliac device according to the present disclosure.
Figure 2A:
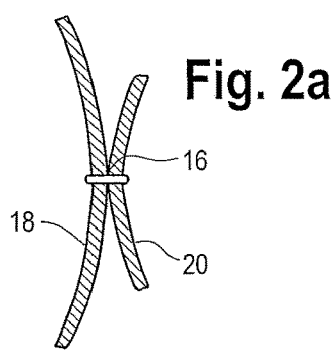
Figure 2B:
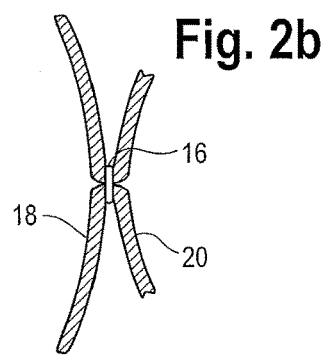
FIG. 2b is a cross-sectional view of the bifurcated iliac device of FIG. 1b.
Figure 3:
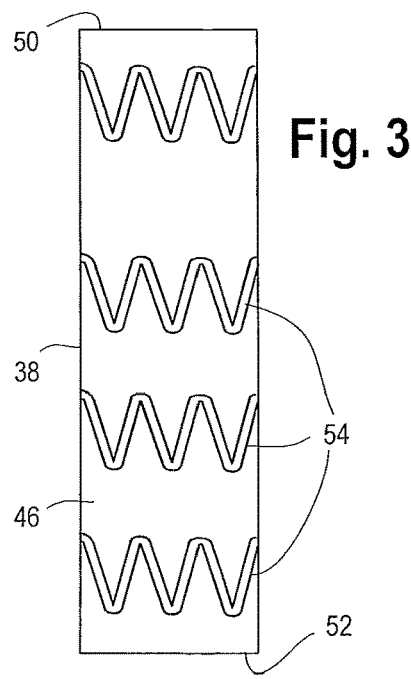
FIG. 3 illustrates one example of a connection stent graft that may sealingly connect at its proximal end with the bifurcated iliac device and extend into an external iliac artery.
Figure 4:
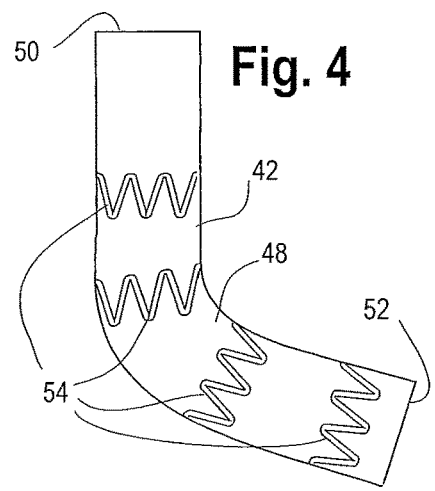
FIG. 4 illustrates one example of a connection stent graft that may sealingly connect at its proximal end with the bifurcated iliac device and extend into an internal iliac artery.

At the distal-most portion 8 of the main body 4 is bifurcation 16. Extending from the body 4 at a bifurcation 16 is a first tubular leg 18 and a second tubular leg 20. In one example, the length of the tubular body portion 4 may be equal to or less than the length of one or both of the tubular legs 18, 20 and/or, in another example, the length of the tubular body portion 4 may be no more than 150% of the length of one or both of the tubular legs 18, 20. While the device 2 bifurcates into the first and second tubular legs 18, 20 distal to bifurcation 16 as shown in FIGS. 1a and 1b, the main tubular body portion 4 located proximal to the bifurcation 16 is preferably non-bifurcated. In other words, the bifurcation preferably does not extend proximally all the way through lumen 10 to proximal end 6 of the device 2.

The first leg 18 preferably includes a proximal end 22 and a distal end 24 and a lumen 26 extending therebetween. The lumen 26 of the first leg 18 is in flow communication with the main lumen 10 of the body portion 4. The first leg 18 may be adapted for placement adjacent to the ostium of the external iliac artery for example, and may have a diameter ranging from about 6 mm to about 14 mm, and preferably about 12 mm. One or more stents 28 may be sutured or otherwise attached to the inside and/or the outside of the first leg 18.

The second tubular leg 20 also preferably includes a proximal end 30 and a distal end 32 and lumen 34 extending therebetween. The lumen 34 of the second leg 20 is in flow communication with the main lumen 10 of the body portion 4. Preferably, the second leg 20 is adapted for placement adjacent to the ostium of the internal iliac artery, and may have a diameter ranging from about 6 mm to about 14 mm, and preferably about 8 mm. One or more stents 36 may be sutured or otherwise attached to the inside and/or the outside of the second leg 20. In one example, the diameter of lumen 10 at the proximal end 6 of the tubular body 4 may be less than the combined diameters of lumens 26 and 34 of the respective first and second legs 18, 20.

The placement of the stents 14, 28, 36 at the upper and lower ends of the bifurcated iliac device 2 provides stability as well as a good sealing surface where the prosthesis can engage the wall of the vessel lumen into which it is inserted or alternatively, engage one or more additional proximally or distally located stent grafts as described below. The stents 14, 28, 36 attached to the body portion 4 and/or the legs 18, 20 may be standard z-stents such as Gianturco Z stents, spiral-z stents, rings or a combination thereof, and may be constructed from various known materials such as Nitinol, stainless steel, and/or other suitable materials.

The bifurcated iliac device 2 may be constructed or sewn in several different ways. In one example, as shown in FIG. 1a the bifurcated portion 16, including the first and second legs 18, 20, could be constructed from two separate pieces of tubular graft material that are attached at their proximal ends 22,30 to the distal end 8 of the main body portion 4. Alternatively, the graft material forming the main tubular body 4 can be cut vertically near the distal end 8 and the respective loose ends of material then sewn along the vertical cut to form the two adjacent, substantially parallel first 18 and second 20 legs. In this way, the distal end 8 of the main body 4 and proximal ends 22, 30 of each of the legs 18, 20 are integral and formed from the same piece of material. In yet another example, as shown in FIG. 1b, a distal portion 8 of the main body lumen 10 could be stitched together such that a "figure-eight" cross section is formed to produce two separate lumens 26, 34. A device 2 with two differently sized lumens could be achieved either by stitching the main body lumen 10 off-center, or by creating two lines of stitches; one line of stitching to divide the distal end 8 of the main body into two equally sized lumens and a second line of stitching to reduce the size of one of the lumens to the desired size.

Figure 5:
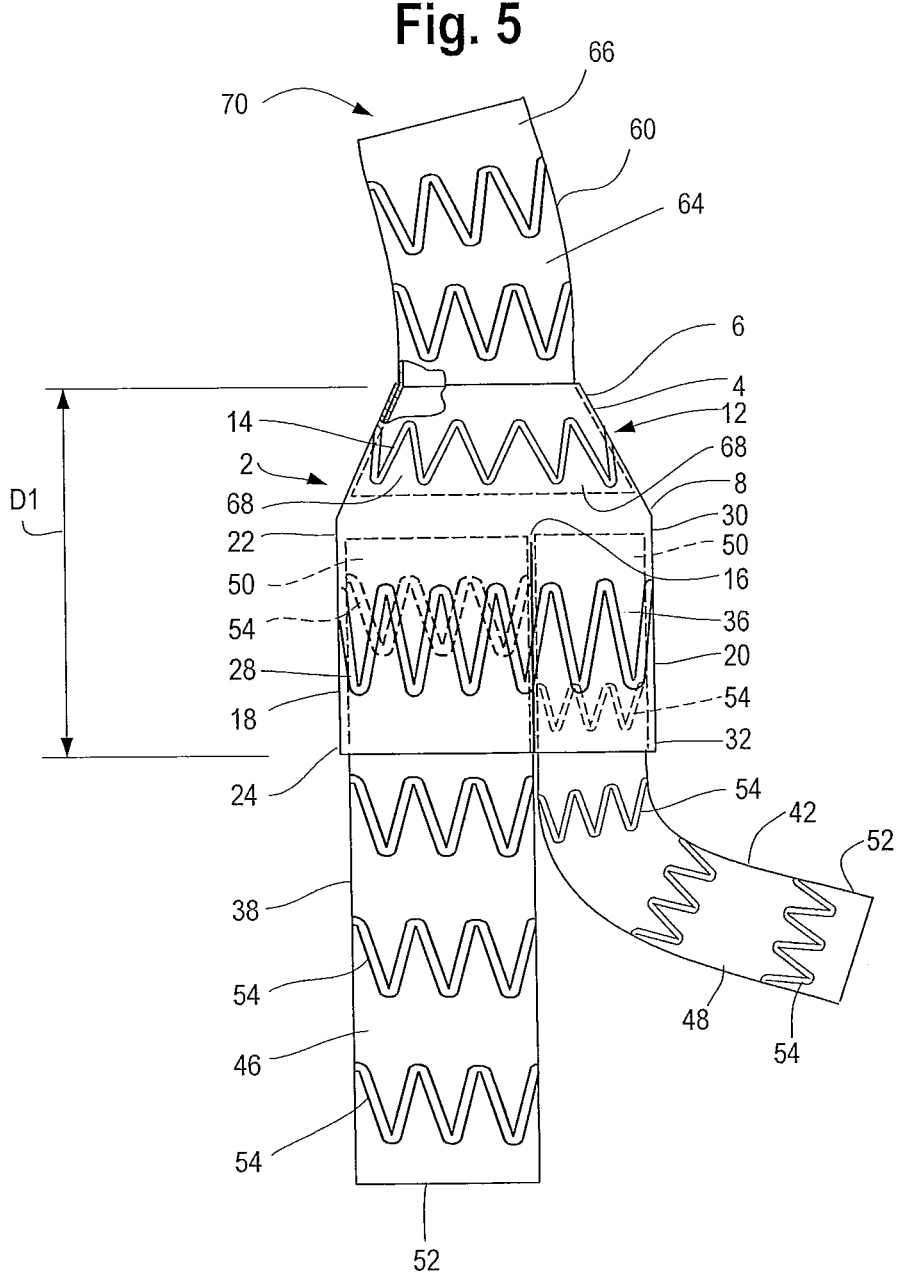
FIG. 5 shows one example of a stent graft assembly including a bifurcated iliac branch device sealingly connected to a proximally located bridging limb. Two connection stent grafts as shown in FIGS. 3 and 4, respectively, extend distally from the assembly.
Figure 6:
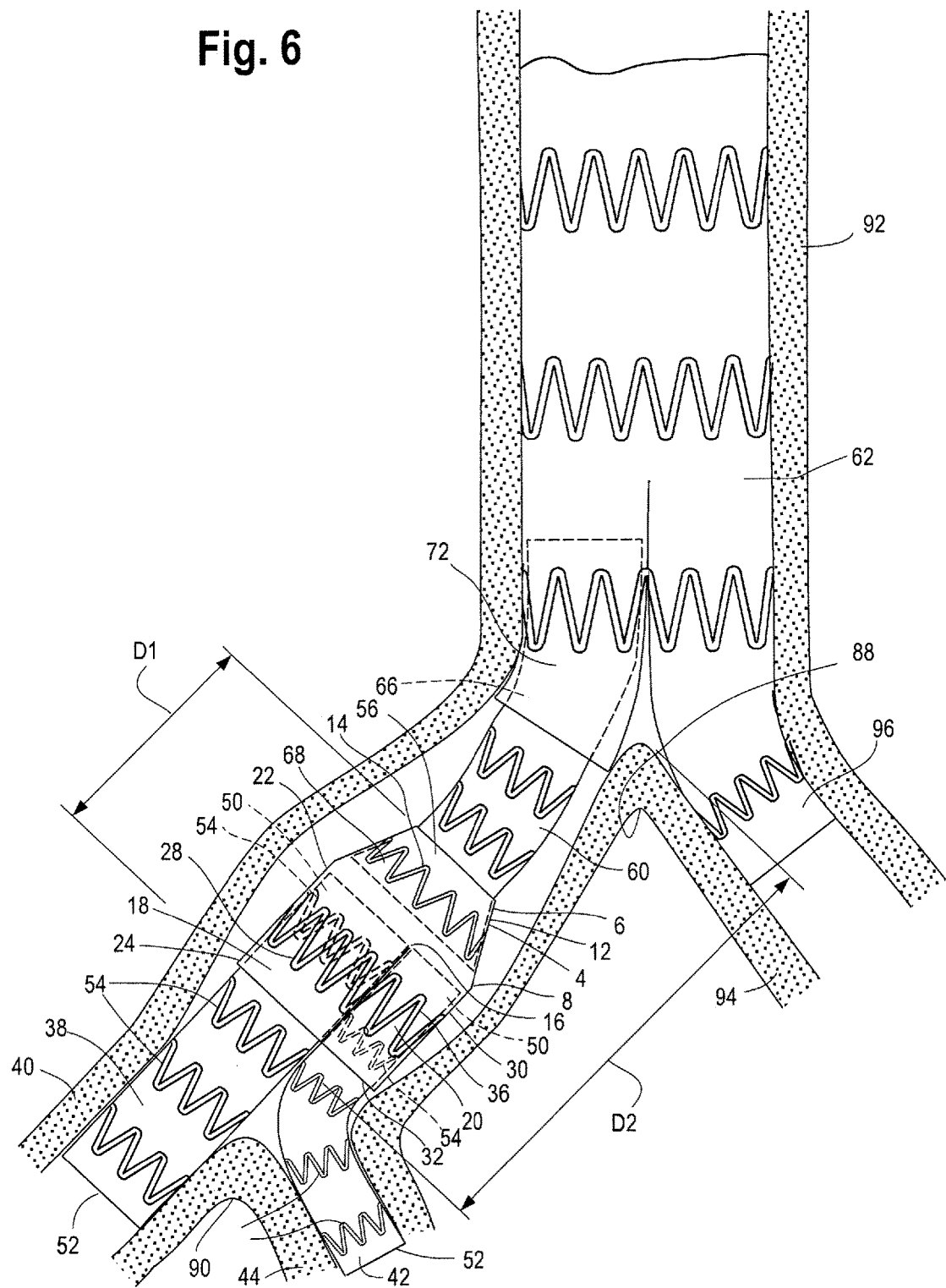
FIG. 6 shows one example of a stent graft assembly as shown in FIG. 5 within the vasculature of a patient having an aneurysm in a common iliac artery.

As shown in FIG. 5, one or more connection stent grafts can be connected to the first and second tubular legs 18, 20, respectively, of the bifurcated iliac device 2. As shown in FIGS. 5 and 6, a first connection stent graft 38 extends distally from the first tubular leg 18 into the external iliac artery 40 and a second connection stent graft 42 extends distally from the second tubular leg 20 into the internal iliac artery 44. As shown in FIG. 5, the connection stent grafts 38, 42 preferably do not extend into the main lumen 10 of the main body portion 4, but if necessary or desired, at least a portion of one or more of the connection stent grafts 38, 42 may extend partially into the main lumen 10. The connection stent grafts 38, 42 preferably each comprise a substantially tubular body 46, 48 having a proximal end 50 and a distal end 52. The proximal end 50 of each of the connection stent grafts 38, 42 may sealingly engage within the "socket" provided by the respective lumens 26, 34 of the first and second tubular legs 18, 20. The overlap between the internal surface or lumen 26, 34 of the leg and external surface of the connection stent graft 38, 42 at its proximal end 50 provides a secure frictional connection therebetween. Alternatively, it is also contemplated that the connection stent grafts 38, 42 may be sealingly connected to the first and/or second tubular legs 18, 20 of the bifurcated device 2 by other acceptable mechanisms. For example, the connection stent grafts 38, 42 may be flared (not shown) at the proximal end 50 to securely anchor the connection stent 38, 42 within the socket or lumen 26, 34 of the tubular legs 18, 20. In such case, the tubular legs 18, 20 may be correspondingly shaped, such as with a distal taper, for sealing engagement with the flared proximal end 50 of the connection stent graft 38, 42. The connection stent graft 38, 42 may also be secured within the socket or lumen 26, 34 of the first and/or second tubular legs 18, 20 by stitching or similar attachment means.

One or more stents 54 may be sutured or otherwise attached to the inside and/or the outside of the connection stent grafts 38, 42 between the proximal 50 and distal ends 52. In one example, the connection stent graft 38, 42 can be balloon expandable or self-expanding. The stents 54 attached to the respective first and second connection stent grafts 38, 42 may be standard z-stents such as Gianturco Z stents, spiral-z stents, rings or a combination thereof, and may be constructed from various known materials such as Nitinol, stainless steel, and/or other suitable materials. As illustrated in FIGS. 5 and 6, the first connection stent graft 38 is sealed into the first tubular leg 18, thus providing patency to the external iliac artery 40, while the second connection stent graft 42 is sealed into the second tubular leg 20, thus providing patency to the internal iliac artery 44.

In other words, a single bifurcated stent graft segment, such as bifurcated device 2, can be positioned in the common iliac artery 56 to provide bifurcated intraluminal flow to be directed to both the internal 44 and external 40 iliac arteries through one or more connection stent grafts 38, 42. A physician is thereby free to choose separate, appropriately sized connection stent grafts 38, 42 of varying diameter and/or length for each of the internal 44 and external 40 iliac arteries, essentially providing a customizable assembly that is based on the unique layout of a particular patient's vasculature and location of aneurysmal portions 58 requiring treatment.

As illustrated in FIG. 1a, one example of the bifurcated iliac device 2 is shown and preferably includes a proximally tapered body portion 4. Preferably, the entire main body portion 4 proximal to the bifurcation 16 may be tapered such that the diameter of the lumen 10 narrows from the bifurcation 16 to the proximal end 10. Alternatively, the main body 4 may include a constant diameter region (not shown) just proximal of the bifurcation 16, and a tapered portion 12 may extend proximally from the constant diameter region to the proximal end 6 of the device 2.

The tapered 12 proximal body portion 4 of the bifurcated iliac 2 device is preferably connected to a second prosthesis 60, such that there exists some overlap between the proximal end 6 of the bifurcated device 2 and the distal end of the second prosthesis 60. In one example, the second prosthesis is a bridging limb 60. As FIG. 6 illustrates, the bridging limb 60 allows the bifurcated iliac device 2 to be in fluid communication to a proximally located third prosthesis 62, such as an AAA bifurcated stent graft, (i.e., a Zenith AAA stent graft; Cook Incorporated, Bloomington, Ind.).

The bridging limb 60 preferably comprises a tubular body 64 of biocompatible graft material having a proximal end 66 and a distal end 68 and a lumen 70 extending therebetween. The bridging limb 60 may be a provided in a variety of shapes, lengths and sizes. For example, the bridging limb 60 may preferably be provided in a range of lengths such that it can adequately bridge the distance between bifurcated iliac device 2 and the AAA stent graft 62. The distal end 68 of the bridging limb may be outwardly flared, such that it generally corresponds to the angulation of the proximal taper 12 of the bifurcated iliac device 2, to thereby provide a mechanical anchor between the proximal end 6 of the bifurcated iliac device 2 and the distal end 68 of the bridging limb 60. However, the bifurcated iliac device 2 may also be sealingly connected to a proximally located second prosthesis 60 by other acceptable methods including friction fit, sutures and the like.

In an alternative example, the tapered proximal body portion 12 of the bifurcated iliac device 2 may be connected directly to a distal end portion of an AAA main graft 62 (thereby eliminating the intermediate bridging limb 60). In such case, the distal end portion of the AAA graft 62 preferably comprises a distal flare like that described above in relation to the bridging limb, 60 which flare is configured to generally match the angulation of the proximal taper 12 of the bifurcated iliac device 2, to thereby provide a mechanical anchor between the proximal end 6 of the bifurcated iliac device 2 and the distal end of the AAA graft 62.

As previously mentioned, the use of a bifurcated iliac device 2 having a reduced overall length increases the patient base able to receive endovascular treatment therewith. In one example, reduction in overall length is achieved by tapering 12 the proximal end 6 of the bifurcated iliac device 2. More specifically, an iliac branch device may typically require about 22 mm of overlap between the proximal end of the iliac branch device and a proximally located second prosthesis such as a bridging limb. Previously, this overlap has been achieved by lengthening the proximal portion of the iliac branch device enough to provide the sufficient surface to overlap and seal with the distal portion of the bridging limb, thereby providing a secure connection between the respective surfaces based on friction alone. The required overlap length at the proximal end of the iliac branch device, however, increases the overall length of the iliac branch device such that it may no longer be suitable for treating patients having anatomical limitations.

By tapering 12 the proximal end portion 6 of the bifurcated iliac device 2, the overall length of the device 2 can be reduced or minimized. For example, the tapered proximal end 12 still provides a sufficient sealing surface adapted for engagement with the distal flare 68 of a proximally located second prosthesis (e.g., a bridging limb 60 and/or AAA main body graft 62), which also serves to mechanically anchor the respective components together in the vasculature. In other words, the proximal taper 12 of the bifurcated iliac device 2 allows the length of the device 2 to be minimized, without sacrificing the strength of the connection between the respective two prostheses (e.g., the iliac branch device 2 and a proximally located prosthesis such as bridging limb 60 and/or AAA graft 62).

It is also contemplated, in yet another example of the bifurcated iliac device 74 illustrated in FIGS. 7-9, that the device 74 may have a relatively constant diameter extending substantially the entire length from a proximal end 76 of the device to the distal end 78. At least one stent 79 may be attached to the graft material, which, as shown in FIG. 7, is preferably an external stent 79 that may be sutured or otherwise attached over at least a portion of the bifurcated area 80 including over a portion of the first and second tubular legs 82-84. In addition to the external stent 79, one or more internal stents within the lumen of the bifurcated device 74 (not shown) may also be provided, as necessary or desired to provide support and stability to the graft. The bifurcated device 74 shown in FIG. 7, having at least one external stent 79, may be used for treatment of isolated iliac aneurysms, with the external stent 79 configured to seal the bifurcated iliac device 74 to a section of healthy tissue in the common iliac artery 86. In other words, it is not necessary to connect the proximal end 76 of the bifurcated iliac device 74 shown in FIG. 7 to a proximally located second prosthesis (such as a bridging limb 60 and/or a AAA bifurcated main graft 62), as the bifurcated iliac device 74 can be directly anchored to a sealing zone of healthy tissue in the common iliac artery 86 as illustrated in FIG. 9.

As such, the length of the bifurcated iliac device 74 (measured from the proximal end 76 to the distal-most end 78 of the tubular legs 82, 84) can be varied as necessary, depending on the geometry of a particular patient's vasculature. Preferably, the overall length of the device can be reduced or otherwise minimized to the extent necessary to allow treatment of a patient base having shortened common iliac arteries 86. The device 74 need only be long enough to provide a surface to which an external stent 79 can be connected (for anchoring the device 74 to a healthy portion of the vasculature) and to provide first 82 and second tubular legs 84 having sufficient length into which one or more connection stents 38, 42 can be sealingly connected (to provide patency to one or both of the external iliac artery 40 and internal iliac artery 44). In other words, the reduction in overall length of the device 74 illustrated in FIG. 7 is accomplished, at least in part, by the fact that the bifurcated iliac device 74 can be anchored directly to healthy tissue within the common iliac artery, and does not require any overlap between a proximal end 76 of the device 74 with the distal end of a proximally located second prosthesis.

As also shown in FIG. 9, a connection stent graft 38, 42 can then be connected to one or both of the first 82 and second tubular legs 84 of the iliac branch device 74. For example, a first connection stent graft 38 can be sealed within the socket or lumen provided by the first tubular leg 82 and extend into the external iliac artery 40. Likewise, a second connection stent graft 42 can be sealed within the socket or lumen provided by the second tubular leg 84 and extend into the internal iliac artery 44. Appropriately sized first and second connection stent grafts 38, 42 can be selected such that they extend distally as far as necessary within the respective external iliac artery 40 and internal iliac artery 44 to seal with healthy tissue, thereby bypassing any aneurysmal area 58.

It will be seen that a stent graft assembly 1, such as that shown in FIG. 5 having the above-described features has an overall reduced length, a dimension that is shown, for example, in FIG. 5, which distance "D1" is measured from a proximal end 6 of the iliac branch device 2 to the furthest distal extent 24, 32 of the tubular legs 18, 20. The assembly 1 may be successfully deployed into an aneurysmal 58 common iliac artery 56 having a particular length, which is the distance "D2" measured from aortic bifurcation 88 down to the proximal side of the ostium of the internal iliac artery 44. The overall reduced length D1 of a stent graft assembly 1 of the type discussed above is preferably less than the distance D2 so that access over the aortic bifurcation 88 is possible to endovascularly enter the proximal end 6 of the device 2 and the second tubular leg 20 that is adjacent the ostium of the IIA 44 to allow cannulation and introduction of a connection stent graft 42 into the internal iliac artery 44.

The length of the connection stent graft 38, 42 is preferably selected such that they can extend to non-aneurysmal region of the external iliac artery 40 and internal iliac artery 44, respectively, so that a seal may be obtained with the distal end 52 of the connection grafts 38, 42 within the arteries as shown in FIG. 6. Where an aneurism 58 extends some distance down the external iliac artery 40, a further leg extension (not shown) may be placed so that it extends through non-aneurysmal region of the external iliac artery 40. The above-described assembly 1 can be inserted sequentially into the vasculature, including into the common 56, internal 44 and external iliac arteries 40, to repair one or more aneurysms formed therein.

FIG. 6 shows one example of a stent graft assembly 1 seated into an aneurysmal common iliac artery 56. The illustrated vasculature generally consists of a aorta 92 extending down to an aortic bifurcation 88 and into the iliac 56 and contra-iliac 94 arteries. The common iliac artery 56 further bifurcates at 90 into an external iliac artery 40 and an internal iliac artery 44. The internal iliac artery 44 is a blind artery, as endovascular access is only available via the common iliac artery 56.

The assembly 1 may be deployed using standard endoluminal techniques. For example, one or more components of the assembly 1 may be may be compressed into a delivery configuration and loaded onto a delivery device, such as an introducer or sheath and deployed using the devices and/or methods described in U.S. Pat. No. 7,435,253 to Hartley et al. and U.S. Pat. No. 7,407,509 to Greenberg et al., which are incorporated by reference herein in their entirety.

In one non-limiting example, the general order of delivery and placement of such a stent graft assembly 1 for treatment of aneurysmal iliac arteries may be as follows. First, the bifurcated iliac device 2 is placed within the common iliac artery 56. In the exemplary device illustrated in FIG. 1a, the entire device 2 may be located within an aneurysmal portion 58 of the common iliac artery 56. Alternatively, with the exemplary device 74 illustrated in FIG. 7, it is preferable that at least a portion of the device 74 is located within a non-aneurysmal portion of the common iliac artery 56 such that the external stent 79 can seal to and anchor the graft 74 to a portion of healthy tissue in the common iliac artery 56 as shown in FIG. 9. It will be appreciated that the device 74 illustrated in FIGS. 7-9 can be placed within the common iliac artery 56 without sealing to another proximally located prosthesis, and therefore, is suitable for treating isolated iliac aneurysms.

Preferably, as shown in FIG. 6, for example, the first tubular leg 18 is adjacent to and faces towards the ostium of the external iliac artery 40, while the second tubular leg 20 is adjacent to and faces towards the ostium of the internal iliac artery 44. Subsequent to placement of the bifurcated iliac device, 2, 74 a connection stent graft 42, which extends down into the internal iliac artery 44, may be placed. A proximal end portion 50 of the connection stent graft 42 is sealingly engaged within the socket or lumen 34 provided by the second tubular leg 20, 84. The connection stent graft 42 extends distally from the second tubular leg 20, 84 such that the distal end of the connection stent graft 42 engages in a sealing manner into a non-aneurysmal portion of the internal iliac artery 44.

The bifurcated iliac device 2 of FIG. 6 is preferably connected to a second, proximally located prosthesis 60. For example, if necessary or desired to treat an aneurysmal portion of the aorta, a main AAA bifurcated stent graft 62, such as the Zenith AAA stent graft (Cook Incorporated, Bloomington, Ind.) may be deployed through the contra-lateral iliac artery 94 so that its longer leg 96 extends down the contra-lateral iliac artery 94 and its shorter leg 72 terminates proximal of the proximal end 6 of the bifurcated iliac device 2 and proximal of the aortic bifurcation 88. A second prosthesis 60, such as a bridging limb 60 having a flared distal end 68 matching the angulation of the proximal taper 12 of the bifurcated iliac device 12 as described above, may be deployed to connect the shorter leg 72 of the main bifurcated AAA stent graft 62 to the proximal end 6 of the bifurcated iliac device 2. Alternatively, the proximal end 6 of the bifurcated iliac device 2 can be connected directly to a distal end of the AAA stent graft 62. In such a case where the bifurcated iliac device 2 is connected directly to a distal end of the AAA graft 62, however, it would be preferable that the device 2 be sealingly connected to the longer leg 96 of the AAA graft 62. Accordingly, the distal end of the longer leg 96 preferably includes a distal flare as described previously to accommodate the angulation of the proximal taper 12 of the bifurcated iliac device 2 and provide a mechanical anchor between the two prostheses.

Another connection stent graft 38 may also be placed which extends down into the external iliac artery 40. Connection stent graft 38 may be placed either before or after the iliac device 2 is connected to a second, proximally located prosthesis 60. As shown in FIG. 6, a proximal end portion 50 of the connection stent graft 38 is sealingly engaged within the socket or lumen 26 provided by the first tubular leg 18 of the bifurcated iliac device 2. The connection stent graft 38 extends distally from the first tubular leg 18 such that the distal end 52 of the connection stent graft 38 engages in a sealing manner into a non-aneurysmal portion of the external iliac artery 40. By this arrangement a stent graft assembly 1 is effectively bridging the aneurysmal regions 58 of the vasculature by sealing in the non-aneurysmal portion of iliac arteries.

It is noted that while the present disclosure generally describes the stent graft assembly 1 in the context of delivery and deployment into the iliac arteries, it is also contemplated that the disclosed assembly and method is also suitable for use in other portions of the vasculature. In one non-limiting example, the assembly may be configured for placement in the aorta and branch vessels extending therefrom such as the brachiocephalic, carotid and/or subclavian arteries. More specifically, the main tubular body 4 of device 2 may be positioned within the aortic arch. The bridging limb 60 may be sealingly connected to the proximal end 6 of the main tubular body, as illustrated in FIG. 5.

In one example, when the main body 4 is positioned within the aorta, the second tubular leg 20 may be preferably located near the greater curve of the aortic arch adjacent the ostium of one or more of the previously mentioned branch vessels extending from the aorta such that when connection stent graft 42 is sealingly connected within the socket provided by the second tubular leg 20, the connection stent graft 42 may extend into a branch vessel extending from the aorta (i.e., brachiocephalic, carotid and/or subclavian arteries). It is also contemplated that the main body 4 of the device 2 may also include additional openings or fenestrations (not shown) formed in the graft material, for one or more additional connection stent grafts 42 to extend therefrom so as to provide flow to more than one branch vessel extending from the aorta simultaneously when the main body 4 is positioned within the aorta.

Throughout this specification, unless the context requires otherwise, the words "comprise" and "include" and variations such as "comprising" and "including" will be understood to imply the inclusion of an item or group of items, but not the exclusion of any other item or group items.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A stent graft assembly comprising:
   a. a first prosthesis comprising:
      i. a main body formed of biocompatible graft material having a proximal end, a distal end, a length from the proximal end to the distal end, and a main lumen extending between the proximal and distal ends, wherein the main lumen comprises a single lumen extending the length of the main body;
      ii. a bifurcated portion extending distally from the main body, the bifurcated portion comprising a first tubular portion defining a first lumen and a second tubular portion defining a second lumen, wherein the first and second lumens are in communication with the main lumen, wherein the bifurcated portion defines a continuous figure eight cross-section from a proximal end of the bifurcated portion to a distal end of the bifurcated portion, wherein the first and second lumens are different sized lumens; and
      iii. wherein the main body portion tapers continuously inwardly from the bifurcated portion to a proximal free end of the main body at a first angulation, wherein the proximal free end of the main body defines a proximal most opening;
   b. a second prosthesis comprising:
      i. a tubular body of biocompatible graft material having a proximal end and a flared distal end portion, the flare tapering outwardly to the distal end at a second angulation;
   c. wherein the flared distal end portion of the second prosthesis overlaps with the tapered main body of the first prosthesis to sealingly engage with the tapered main body of the first prosthesis;
   d. a third prosthesis configured to receive the second prosthesis in an overlapping relationship comprising:
      i. a main body formed of biocompatible graft material having a proximal end and a distal end and a main lumen extending therebetween wherein the main lumen comprises a single lumen extending the length of the main body;
      ii. a bifurcated portion including two limbs extending distally from the main body, the bifurcated portion comprising a first tubular portion defining a first lumen and a second tubular portion defining a second lumen, wherein the first and second lumens are in communication with the main lumen, wherein each of the two limbs has a distal end opening; and iii. wherein a distal end opening of one of the limbs is configured to receive the proximal end of the second prosthesis.

2. The assembly of claim 1 wherein the first angulation of the distal flare of the second prosthesis substantially corresponds to the second angulation of the taper of the main body of the first prosthesis.

3. The assembly of claim 1 wherein the first prosthesis is configured to be deployed in a common iliac artery, wherein the first tubular portion of the first prosthesis is configured to face an ostium of an external iliac artery and the second tubular portion of the first prosthesis is configured to face an ostium of an internal iliac artery.

4. The assembly of claim 1 wherein the first tubular portion of the first prosthesis defines a socket for receiving a first connection stent graft.

5. The assembly of claim 4 wherein the first connection stent graft is adapted for placement in an external iliac artery.

6. The assembly of claim 1 wherein the second tubular portion of the first prosthesis defines a socket for receiving a second connection stent graft.

7. The assembly of claim 6 wherein the second connection stent graft is adapted for placement in an internal iliac artery.

8. A method for treating a diseased vessel comprising an aorta branching into first and second common iliac arteries, the method comprising:
   a. introducing a first prosthesis into a patient's vasculature, the first prosthesis comprising:
      i. a main body formed of biocompatible graft material having a proximal end and a distal end and a main lumen extending therebetween wherein the main lumen comprises a single lumen extending the length of the main body;
      ii. a bifurcated portion including two limbs extending distally from the main body, the bifurcated portion comprising a first tubular portion defining a first lumen and a second tubular portion defining a second lumen, wherein the first and second lumens are in communication with the main lumen, wherein each of the two limbs has a distal end opening;
   b. positioning the first prosthesis such that the main body of the first prosthesis resides in the aorta and one or both of the limbs resides in a respective common iliac artery;
   c. introducing a second prosthesis into a patient's vasculature, the second prosthesis comprising:
      i. a main body formed of biocompatible graft material having a proximal end, a distal end, a length from the proximal end to the distal end, and a main lumen extending between the proximal and distal ends, wherein the main lumen comprises a single lumen extending the length of the main body;
      ii. a bifurcated portion extending distally from the main body, the bifurcated portion comprising a first tubular portion defining a first lumen and a second tubular portion defining a second lumen, wherein the first and second lumens are in communication with the main lumen, wherein the bifurcated portion defines a continuous figure eight cross-section from a proximal end of the bifurcated portion to a distal end of the bifurcated portion and defines two different sized lumens; and
      iii. wherein the main body portion continuously tapers inwardly from the bifurcated portion to a proximal free end of the main body, wherein the proximal free end of the main body defines a proximal most opening;
   d. positioning the second prosthesis in a common iliac artery;
   e. introducing a third prosthesis into the patient's vasculature, the third prosthesis comprising a tubular body of biocompatible graft material having a cylindrical proximal end and a flared distal end, the flare tapering outwardly to the distal end;
   f. sealingly connecting the tapered main body of the second prosthesis and the flared distal end of the third prosthesis, such that the flared distal end portion of the third prosthesis overlaps with the tapered main body of the second prosthesis to sealingly engage with the tapered main body of the second prosthesis; and
   g. sealingly connecting the cylindrical proximal end of the third prosthesis with a limb of the first prosthesis in an overlapping relationship.

9. The method of claim 8 further comprising, prior to the step of introducing the third prosthesis;
   a. introducing a first connection stent graft into the internal iliac artery;
   b. sealingly connecting a proximal end portion of the first connection stent graft and the second tubular portion of the second prosthesis.

10. The method of claim 9 further comprising:
    a. introducing a second connection stent graft into the external iliac artery;
    b. sealingly connecting a proximal end portion of the second connection stent graft and the first tubular portion of the second prosthesis.

* * * * *